(12) United States Patent
Spielberg et al.

(10) Patent No.: US 11,617,795 B2
(45) Date of Patent: Apr. 4, 2023

(54) PHARMACEUTICAL SYRUP FORMULATION OR SUSPENSION

(71) Applicants: Max Spielberg, Miami, FL (US); David Johnson, Beverly Hills, CA (US)

(72) Inventors: Max Spielberg, Miami, FL (US); David Johnson, Beverly Hills, CA (US)

(73) Assignee: Genexa Inc., Atlanta, GA (US)

( * ) Notice: Subject to any disclaimer, the term of this patent is extended or adjusted under 35 U.S.C. 154(b) by 0 days.

(21) Appl. No.: 17/817,637

(22) Filed: Aug. 4, 2022

(65) Prior Publication Data

US 2023/0071165 A1    Mar. 9, 2023

Related U.S. Application Data

(63) Continuation of application No. 17/342,414, filed on Jun. 8, 2021, which is a continuation-in-part of application No. 16/827,529, filed on Mar. 23, 2020, now abandoned, which is a continuation of application No. 15/912,785, filed on Mar. 6, 2018, now Pat. No. 10,596,266.

(60) Provisional application No. 62/580,648, filed on Nov. 2, 2017.

(51) Int. Cl.

| | | |
|---|---|---|
| A61K 31/00 | (2006.01) |
| A61K 47/46 | (2006.01) |
| A61K 9/00 | (2006.01) |
| A61K 36/88 | (2006.01) |
| A61K 35/644 | (2015.01) |
| A61K 36/736 | (2006.01) |
| A61K 36/35 | (2006.01) |
| A61P 11/14 | (2006.01) |
| A61K 36/235 | (2006.01) |
| A61K 47/26 | (2006.01) |
| A61K 36/9068 | (2006.01) |
| A61K 47/12 | (2006.01) |
| A61K 36/9066 | (2006.01) |
| A61K 36/074 | (2006.01) |
| A61K 31/167 | (2006.01) |

(52) U.S. Cl.
CPC .............. *A61K 47/46* (2013.01); *A61K 9/0053* (2013.01); *A61K 9/0095* (2013.01); *A61K 31/167* (2013.01); *A61K 35/644* (2013.01); *A61K 36/074* (2013.01); *A61K 36/235* (2013.01); *A61K 36/35* (2013.01); *A61K 36/736* (2013.01); *A61K 36/88* (2013.01); *A61K 36/9066* (2013.01); *A61K 36/9068* (2013.01); *A61K 47/12* (2013.01); *A61K 47/26* (2013.01); *A61P 11/14* (2018.01)

(58) Field of Classification Search
CPC ..................................................... A61K 31/00
See application file for complete search history.

(56) References Cited

PUBLICATIONS

Paul et al., "Placebo effect in the treatment of acute cough in infants and toddlers, a randomized clinical trial," JAMA Pediatrics 168(12):1107-1113, 2014.*

* cited by examiner

*Primary Examiner* — Rosanne Kosson
(74) *Attorney, Agent, or Firm* — Greenberg Traurig LLP; Nigamarayan Acharya

(57) ABSTRACT

A stable pharmaceutical formulation or suspension has a pharmaceutical active agent, agave, and a dilutant. The formulation or suspension has viscosity suitable for drinking.

24 Claims, No Drawings

PHARMACEUTICAL SYRUP FORMULATION OR SUSPENSION

TECHNICAL FIELD

This application relates to aqueous suspensions and formulations. This application also relates to a pharmaceutical suspension composed of pharmaceutical active agents, suspension agents, sweetening agents and flavoring agents.

BACKGROUND

Children and older persons can have problems swallowing tablets or capsules. In these situations, it is desirable to provide drugs either in a chewable solid form or in a liquid form/syrup. It is not an uncommon practice for a parent to prefer giving the sick children, usually those below the age of 12, syrup instead of tablets. Syrups are suited for children. The dose is in volumes and often can be tailored to the child's body weight. Many syrups can be flavored, which improves intake and compliance by children.

One problem is that liquids containing analgesic, antihistamine, and diuretic active pharmaceutical agents taste terrible and pharmaceutical chemists have turned to unnatural and artificial ingredients to mask the taste. No liquid medium, primarily of natural ingredients, containing this combination of active agents are available.

Accordingly, there is a need for an improved pharmaceutical suspension or syrup formulation.

SUMMARY

One aspect includes a stable, pharmaceutical syrup formulation or suspension for oral administration having one or more pharmaceutical active agents, agave syrup, and a dilutant. The syrup formulation can have a viscosity of less than 1500 centipoise at 22 degrees.

Another aspect includes a stable, pharmaceutical syrup formulation or suspension for oral administration having a pharmaceutical active agent, agave syrup, acidic preservative, a sweetening agent, a flavoring agent, and a dilutant. The syrup formulation can have a viscosity of less than 1500 centipoise at about 22 degrees.

Another aspect includes a pharmaceutical suspension that can enhance the taste masking of unpalatable pharmaceutical active agents with generally natural ingredients. One embodiment includes the use of clean inactive ingredients that are gluten-free, non-GMO, and certified vegan. Other embodiments may exclude unnatural ingredients such as aspartame, carbomer, EDTA, gelatin, milk, parabens, polyethylene glycol, titanium dioxide, and other unnatural ingredients.

Another aspect includes pharmaceutical suspensions made with the same active ingredients needed for a treatment, but without the artificial not needed.

Another aspect includes a suspension that can be used as a formulation of pharmaceutical suspension. The following pharmaceutical active agents are suitable for use with the suspension including but not limited to acetaminophen, ibuprofen, famotidine, pseudoephedrine, hydrochloride, chlorpheniramine maleate, dextromethorphan hydrobromide, guaifenesin, diphenhydramine hydrochloride, loperamide hydrochloride, and simethicone and suitable combinations thereof.

DETAILED DESCRIPTION

This application provides a pharmaceutical suspension or syrup formulation that can be used with various active pharmaceutical agents. In one embodiment, a pharmaceutical syrup formulation for oral administration includes one or more pharmaceutical active agents, agave syrup, and a dilutant. A pharmaceutical syrup formulation for oral administration can also include an acidic preservative, a sweetening agent, and a flavoring or masking agent. The term "agave syrup" is referred to as a processed juice obtained from the agave sp. plant (e.g. also referred to as processed sap or processed aguamiel). The term "syrup" means a formulation that has a flow without applied pressures and is sticky or tacky to the touch.

The syrup can have a viscosity of the type used with pharmaceutical suspensions or syrup formulations. The syrup can have a viscosity of between about 200 and 3500 centipoise at about 2.5 rpm to about 30 rpm as determined by a Brookfield Viscometer at about 22 degrees. Further, the syrup can have a viscosity of between about 350 and about 1500 centipoise. For example, the syrup formulation can a viscosity of about 1500 centipoise at about 22 degrees. For example, the syrup formulation has a viscosity of about 1000 centipoise at about 22 degrees. For example, the syrup formulation has a viscosity of about 600 centipoise at about 22 degrees. In many examples, the viscosity of the syrup can be less than 2000 centipoise, less than 1750 centipoise, less than 1500 centipoise, less than 1000 centipoise, less than 750 centipoise, less than 600 centipoise, or less than 500 centipoise.

In one embodiment, the pharmaceutical suspension or syrup formulation can be used to administer pharmaceutical active agents with generally natural ingredients. For example, a pharmaceutical suspension can include the use of clean inactive ingredients that are gluten-free, non-GMO, and certified vegan. Other embodiments may exclude ingredients such as aspartame, carbomer, EDTA, gelatin, milk, parabens, polyethylene glycol, titanium dioxide, and other unnatural ingredients. Certain embodiments can be designed to provide pharmaceutical suspensions made with the same active ingredients needed for a treatment, but without the artificial ingredients.

In another embodiment, a pharmaceutical suspension or syrup formulation includes between 0.01 to 4 w/w % of one or more active pharmaceutical agents, 0.01 and 1% w/w % of an acidic preservative, 0.05 to 5 w/w % of a sweetening agent or flavoring agent, 50% to 98% agave syrup, and water. In one example, the one or more active pharmaceutical agents can be one of the following active agents: dextromethorphan hydrobromide, guaifenesin, or acetaminophen.

In one embodiment, a pharmaceutical suspension includes between 0.5 to 2 w/w % of one or more active pharmaceutical agents, 65% to 98% agave syrup, and water.

In one embodiment, a pharmaceutical suspension includes between 0.5 to 2 w/w % of one or more active pharmaceutical agents, 0.5 and 2% w/w % of an acidic preservative, 1 to 3 w/w % of a sweetening agent or flavoring agent, 75% to 95% agave syrup, and water.

The amount of water or dilatant in the suspension may be reduced to optimize the formulation. The amount of the pharmaceutical active agent dissolved in the suspension can be reduced. This reduction in amount dissolved reduces the need for taste masking. Since, the pharmaceutical active agent remains in the solid (undissolved) form, the pharmaceutical is less likely to be tasted while in the mouth.

The pH of the pharmaceutical suspension or syrup formulation can range from about 4 to about 10. In certain examples, the pH of the suspension can be in the range from 4 to 8. The suspension can be buffered to maintain the pH of the suspension in the desired pH range. Suitable buffers that are not chemically reactive with the other ingredients may be present in the suspension in amounts enough to provide the desired degree of pH buffering. The buffers can range from 0.01 to 1 gram per 100 mL of the suspension. In one example, the acidic preservative can be adjusted to keep the pH of the suspension at a desired level.

In one embodiment, the pharmaceutical suspension or syrup formulation may include about 0.1 to 5 grams of a pharmaceutical active agent per 100 mL of suspension. The amount of the pharmaceutical active agent in the suspension should be enough to provide a therapeutic amount of the pharmaceutical active agent and a convenient dosage unit. Up to about 0.01 to 2 grams pharmaceutical active per 100 mL may be readily included in the suspension system. However, this may vary depending on the pharmaceutical active agent and amounts are known to those with ordinary skill in the art or are readily available or can be determined using pharmaceutical science.

The water added to the pharmaceutical suspension or syrup formulation should be kept at a minimum, to facilitate masking the bitter taste of acetaminophen. The acetaminophen suspension should contain in the range from about 0.1 to 2 grams of water per 100 ml of suspension.

The suspension can be used as a formulation of a pharmaceutical suspension. The following pharmaceutical active agents are suitable for use with the inventive suspension including but not limited to acetaminophen, ibuprofen, famotidine, pseudoephedrine, hydrochloride, chlorpheniramine maleate, dextromethorphan hydrobromide, guaifenesin, diphenhydramine hydrochloride, loperamide hydrochloride, and simethicone and suitable combinations thereof. In one embodiment, the pharmaceutical active agents are water soluble or hydrophilic.

Therapeutic combinations of pharmaceutical active agents can include combinations of acetaminophen, ibuprofen or famotidine with pseudoephedrine hydrochloride, chlorpheniramine maleate, astemizole, terfenadine, dextromethorphan hydrobromide, guaifenesin or diphenbydramine for formulations of cold or sinus medication. Acetaminophen, ibuprofen and famotidine could also be combined with antacids to control the gastric irritation caused by these analgesics.

In one embodiment, the pharmaceutical suspension or syrup formulation can effectively mask the bitter taste of pharmaceuticals contained in the suspension. Masking the flavor of bitter pharmaceuticals may be accomplished by using flavoring agents to overpower the bitter flavor of the pharmaceutical. The bitter flavor also can be minimized by limiting the amount of water present in the suspension. Suitable sweetening agents include but are not limited to sugars such as monosaccharides, disaccharides and polysaccharides. Examples of suitable sugars include but are not limited to xylose, ribose, glucose, mannose, fructose, dextrose, sucrose, and maltose, and sugar alcohols such as sorbitol, xylitol, mannitol, glycerin and combination thereof. Presently preferred as a sugar sweetener is fructose provided as an aqueous solution. The amount of sugar sweetener used in the suspension will vary depending on the degree of sweetening desired for the suspension. Generally, the amount of sugar sweetener will be in the range of from about 0 grams to about 1 gram of sugar sweetener per 100 mL of the suspension.

Flavoring agents also may be added to the pharmaceutical suspensions or syrup formulations to improve the palatability of the suspension. Examples of suitable flavoring agents include natural and artificial flavors such as mints (i.e., peppermint, etc.,), menthol, cinnamon, vanilla, artificial vanilla, chocolate, artificial chocolate, both natural and artificial fruit flavors (i.e., cherry, grape, orange, strawberry, etc.,) and combinations of two or more thereof. Flavoring agents are generally provided as a minor component of the suspension in amounts effective to provide a palatable flavor to the suspension. However, flavoring agents are generally present in the suspension in amounts in the range of from about 0 grams to about 5 grams per 100 mL of the suspension.

Optimum masking of the taste of the pharmaceutical active agents in the pharmaceutical suspension or syrup formulation can be achieved by limiting the amount of water in the suspension. As a minimum, the amount of water present in the suspension may be limited to that amount necessary to hydrate the agave syrup. The minimum amount of water also must provide the suspension with enough aqueous base to impart the desired degree of viscosity. For example, if agave syrup is used in the suspension as a sweetener, the total amount of water contained in the suspension be in the range of about 5 to 20 grams per 100 mL of suspension. Accordingly, if a bitter or unpalatable pharmaceutical active is present in the suspension, the amount of water in all the ingredients should be kept to a minimum.

Wetting agents also may be employed in the inventive suspension to facilitate the dispersion of hydrophobic pharmaceutical active agents. The concentration of wetting agents in the suspension should be selected to achieve optimum dispersion of the pharmaceutical active within the suspension with the lowest feasible concentration of wetting agent. It should be appreciated that an excess concentration of wetting agent may cause the suspension to flocculate. Those skilled in the art are well versed in suitable empirical methods to determine the appropriate wetting agents and concentrations to achieve optimum dispersion and avoid flocculation.

Coloring agents, while not generally used and are generally not preferred, can be incorporated in the suspension to provide an appealing color to the suspension. The coloring agents should be selected to avoid chemical incompatibilities with the other ingredients in the suspension. Suitable coloring agents for use in pharmaceutical suspensions are well known to those skilled in the art.

In one embodiment, the pharmaceutical suspension or syrup formulation can be prepared by mixing one or more active agents with agave and then adding water to achieve a desired consistence. One method of making a pharmaceutical syrup formulation for oral administration can include adding an amount of agave into a vessel; warming the amount of the agave in the vessel; adding an amount of one or more pharmaceutical agents to the warmed agave in the vessel; stirring the contents of the vessel until the contents are mixed; adding diluent through the process to achieve a desired viscosity of less than, e.g., 1500 centipoise, 1000 centipoise, 600 centipoise, or 400 centipoise.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

EXAMPLES

The invention will now be illustrated by examples. The examples are not intended to be limiting of the scope of the present invention but read in conjunction with the detailed and general description above, provide further understanding of the present invention and an outline of a preferred process for preparing the compositions of the invention.

Example 1

Acetaminophen Suspension

| Ingredient | Function | Amount (w/w %) |
|---|---|---|
| Pharmaceutical Active Agent (e.g., Acetaminophen) | Treatment | 1.8 |
| Agave syrup | Base | 92 |
| Citrus acid extract | Preservative | 0.20 |
| Masking Agent/Blueberry | Flavoring | 0.60 |
| Water | Diluent | Remaining |

In Example 1, the citrus acid extract and masking agent are optional and are not needed for a suitable or usable formulation.

Example 2

Preparation of Suspension 100 mg of active agent can be added to 100 mL of agave (heated). The mixture is stirred, and water can is added to achieve a desired consistency. Other agents such as sweetening agent and flavoring agent can be added to the suspension.

The invention claimed is:

1. A pharmaceutical syrup formulation for oral administration comprising:
    (a) acetaminophen,
    (b) agave syrup, and
    (c) a diluent, wherein the syrup formulation has a viscosity of less than 1500 centipoise at about 22 degrees; wherein the acetaminophen is suspended in the syrup; and wherein the syrup is palatable.

2. The pharmaceutical syrup formulation of claim 1, wherein the syrup formulation has a viscosity of less than 1000 centipoise at about 22 degrees.

3. The pharmaceutical syrup formulation of claim 1, wherein the syrup formulation has a viscosity of less than 750 centipoise at about 22 degrees.

4. The pharmaceutical syrup formulation of claim 1, wherein the syrup formulation has a viscosity of less than 600 centipoise at about 22 degrees.

5. The pharmaceutical syrup formulation of claim 1, wherein 0.01 to 2 grams of acetaminophen is suspended per 100 mL of the syrup.

6. The pharmaceutical syrup formulation of claim 1, wherein 0.01 to 1 grams of acetaminophen is suspended per 100 mL of the syrup.

7. A stable pharmaceutical syrup formulation for oral administration comprising:
    (a) acetaminophen;
    (b) agave syrup;
    (c) acidic preservative;
    (d) a flavoring agent, and
    (e) a diluent, wherein the syrup formulation has a viscosity of less than 1500 centipoise at about 22 degrees, and wherein the acetaminophen is suspended in the syrup.

8. The pharmaceutical syrup formulation of claim 7, wherein the acetaminophen is between 0.01 to 2% of the formulation by weight.

9. The pharmaceutical syrup formulation of claim 7, wherein the diluent is about 5% of the formulation by weight.

10. The pharmaceutical syrup formulation of claim 7, wherein the agave syrup is less than 98% of the formulation by weight.

11. The pharmaceutical syrup formulation of claim 7, wherein the agave syrup is less than 95% of the formulation by weight.

12. The pharmaceutical syrup formulation of claim 7, wherein the diluent is water.

13. The pharmaceutical syrup formulation of claim 7, wherein the agave syrup is about 95% of the formulation by weight.

14. The pharmaceutical syrup formulation of claim 13, wherein the acidic preservative comprises citric acid.

15. The pharmaceutical syrup formulation of claim 7, wherein the composition is a medicinal preparation formulated as a syrup; and wherein the composition has a viscosity from about 1500 centipoise to about 400 centipoise at about 22 degrees.

16. The pharmaceutical syrup formulation of claim 7, wherein the formulation is orally administered for veterinary and human use.

17. The pharmaceutical syrup formulation of claim 7, wherein the flavoring agent is a bitter-taste-blocking ingredient.

18. A stable, palatable pharmaceutical syrup formulation for oral administration consisting essentially of:
    (a) a therapeutically effective amount of acetaminophen;
    (b) agave syrup;
    (c) acidic preservative;
    (d) a flavoring agent, and
    (e) a diluent, wherein the syrup formulation has a viscosity of less than 1500 centipoise at about 22 degrees and the acetaminophen is suspended in the syrup.

19. The formulation of claim 18, wherein the pharmaceutical syrup formulation has a viscosity of less than 1000 centipoise at about 22 degrees.

20. The formulation of claim 18, wherein the pharmaceutical syrup formulation has a viscosity of less than 1500 centipoise at about 22 degrees.

21. The formulation of claim 18, wherein the pharmaceutical syrup formulation has a viscosity of less than 1500 centipoise at about 22 degrees.

22. The formulation of claim 18, wherein the agave syrup is less than 98% of the formulation by weight.

23. The formulation of claim 18, wherein the agave syrup is less than 95% of the formulation by weight.

24. The formulation of claim 18, wherein the agave syrup is about 95% of the formulation by weight.

* * * * *